United States Patent [19]
Grotz

[11] Patent Number: 5,295,784
[45] Date of Patent: Mar. 22, 1994

[54] SUCTION DEVICE, ESPECIALLY FOR USE IN DENTISTRY

[75] Inventor: Uwe Grotz, Leinfelden-Echterdingen, Fed. Rep. of Germany

[73] Assignee: Durr Dental GmbH & Co. KG, Bietigheim-Bissingen, Fed. Rep. of Germany

[21] Appl. No.: 930,893

[22] Filed: Aug. 17, 1992

[30] Foreign Application Priority Data

Aug. 24, 1991 [DE] Fed. Rep. of Germany ....... 4128150

[51] Int. Cl.⁵ .............................................. F04D 5/00
[52] U.S. Cl. ................... 415/55.6; 415/55.7; 415/59.1
[58] Field of Search ............. 415/55.1, 55.6, 55.7, 415/59.1, 79, 207

[56] References Cited

U.S. PATENT DOCUMENTS

| | | | |
|---|---|---|---|
| 3,315,607 | 4/1967 | MacInnes | 415/55.6 |
| 3,324,799 | 6/1967 | Terrano | 415/55.6 |
| 3,614,256 | 10/1971 | Sieghartner | 415/55.6 |
| 3,661,474 | 5/1972 | Sieghartner | 415/55.6 |
| 3,694,101 | 9/1972 | Rumsey | 415/55.6 |
| 3,761,203 | 9/1973 | Neidhardt et al. | 415/55.6 |
| 4,483,656 | 11/1984 | Abe et al. | 415/55.1 |

Primary Examiner—Edward K. Look
Assistant Examiner—Michael S. Lee
Attorney, Agent, or Firm—Fred Philpitt

[57] ABSTRACT

A two-stage side-channel compressor has in the central portion of its rotor (24) vanes (64) forming a radial compressor stage which allow a first side-channel (44) placed radially outward to be connected to an intake (18) on the central axis of the casing without any increase in the dimensions of the casing and without any loss of pressure.

7 Claims, 7 Drawing Sheets

SUCTION DEVICE, ESPECIALLY FOR USE IN DENTISTRY

The invention relates to a suction device, especially for use in dentistry.

BACKGROUND

In known suction devices of this type, operating on the side-channel compressor principle, the intake orifice and the outlet orifice of the casing are on the edge of the casing, specifically at the ends of the side channel arrangement which runs in the direction of the circumference and is aligned radially with the location of the side-channel compressor vanes. For many applications, and especially for use in dentistry, it would be desirable to have available a suction device of this kind in which the intake orifice is on the central axis of the casing. Such a suction device combined with another unit, such as a separator for liquids, could form a very compactly built unit in its radial dimension. If one were simply to provide such a channel in the casing, leading in a radial direction from a central intake orifice to the intake end of the side channel arrangement, then this would have to be enlarged in its axial dimensions and there would be losses in efficiency due to the sharp diversion of the airstream.

SUMMARY OF THE INVENTION

The present invention therefore aims to provide a suction device, which has a central casing intake orifice without the axial dimensions being altered, and whose suction capacity is not diminished as compared with a machine with an intake orifice on its edge and in alignment with the side channel arrangement.

In the suction device in accordance with the invention, the section of the rotor disposed radially inside the side-channel compressor vanes is formed as a further compressor stage feeding into the intake of the side-channel compressor, this stage effecting the diversion of the airstream and compensating or even overcompensating for the loss of efficiency caused by the diversion of the airstream. Since this additional compressor stage is placed in the central area of the rotor which is usually not utilized, it does not require any additional space. The cost of this additional compressor stage is also low.

The further feature of the invention in accordance with another embodiment is advantageous with regard to the concentration of the radial throughput of air and the creation of an additional difference in pressure in the additional compressor stage provided on the intake side.

If the radial compressor vanes are constructed according to another embodiment, a particularly high degree of efficiency is achieved in this first compressor stage.

In accordance with another embodiment, the combination of a two-stage side-channel compressor with an additionally provided compressor stage on the intake side according to the invention can be achieved in a particularly compact and low-cost form.

A further feature of the invention in accordance with another embodiment serves the purpose of increasing the suction capacity without increasing the structural size of the suction device.

In accordance with another embodiment, one can achieve a compact and geometrically simple channel layout in the casing of the suction device.

In a suction device in accordance with another embodiment, one can achieve a limitation of the pressure produced at the intake orifice when there is only a small throughput.

A further feature of the invention in accordance with another embodiment offers advantages with regard to constant withdrawal of air in the direction of the circumference from the additional compressor vanes provided in the central part of the rotor.

In a suction device in accordance with another embodiment one has a large suction cross-section with a small diameter of the intake orifice since the latter does not have the shaft passing through it.

In accordance with another embodiment one can produce suction devices of differing performance using the same casing, since one can fit power units with different outputs into the casing by varying the amount machined from the locating ribs.

BRIEF DESCRIPTION OF THE DRAWINGS

The invention is explained more fully below with the aid of a constructional example and with reference to the drawings. These show.

DESCRIPTION OF PREFERRED EMBODIMENTS

The drawings show a side-channel suction device for dental applications generally indicated at 10, with a casing which has an upper part 12 as well as a dish-shaped lower part 16 with a peripheral wall 14. Lower part 16 carries a short central intake tube 18 which is connected to the outlet of a separator unit 20 only indicated at 20 by dashes. The latter separates liquid and solid components from the air coming from the dentist's workplace, so that the suction device 10 is only fed with dry air.

The casing parts 12 and 16 enclose between them a pump chamber 22 in which a rotor 24 rotates.

The rotor 24 is overhung mounted on the end of a motor shaft 26, which belongs to an electric motor 28 mounted on the top of the upper part of the casing 12. The upper part of its motor casing is marked 30. An upper end section of the motor shaft 26 carries a fan rotor 32. An outer casing 34 is placed on radial ribs in the part 30 of the motor casing which conducts the airstream created by the fan rotor 32 over the outer surface of the part 30 of the motor casing.

Figure 10:
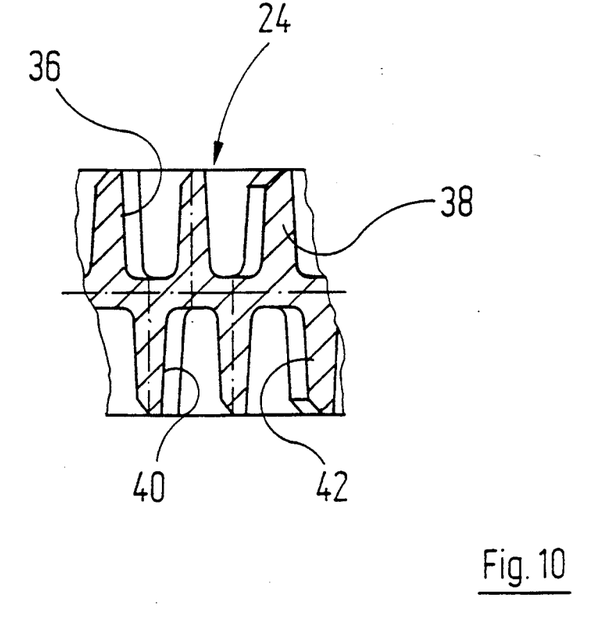
FIG. 10: an axially parallel partial section through the rotor of the suction device along the section line x—x in FIG. 9.

The rotor 24 has two faces that are parallel. Pockets 36 with radially semicircular cross-section are cut in the peripheral area of the upper face, between which side-channel compressor vanes 38 are left. Aligned with these but offset by half a pitch (cf. FIG. 10), pockets 40 are cut in the peripheral area of the lower face of the rotor 24, between which side-channel compressor vanes 42 are left. As can be seen from FIG. 10, the rear end seen in the direction of rotation of the faces of the compressor vanes 38 is formed in each case sloping back at 45 degrees, diagonally to the central plane of the rotor 24.

A first side channel 44, whose angular dimension is about 300 degrees, is formed in the bottom of the upper part 12 of the casing in alignment with the path of the compressor vanes 38. The side channel 44 has an outlet section 46 running radially diagonally outward, which is connected to an axial connecting channel 48 in the central part 14 of the casing and leads to a diagonal, substantially radially directed intake section 50 of a second side channel 52, which is provided in the top of the lower part 16 of the casing and is in alignment with the path of the compressor vanes 42. The peripheral dimension of the side channel 52 is about 300 degrees. An outlet section 54 of the side channel 52 is connected to an outlet tube 56 of the lower part 16 of the casing.

A silencer 58 is inserted in the latter, which is surrounded by a silencer casing 60 with an outlet orifice which is only indicated diagrammatically and is connected to an exhaust passage in the main structure.

In a central part of the rotor 24, compressor vanes 64 curved in the direction of rotation are provided which are covered by a curved rotationally symmetrical guide wall 66 whose end section on the intake side is axially parallel, while its outlet section is positioned at only a slight angle to a transverse plane. The lower faces of the compressor vanes 64 slope inward from the edge to a hub section 68 of the rotor 24. The intake end of the guide wall 66 is flush with the upper edge of a conical intake orifice 70 in the casing, which is provided in the bottom of the lower part 16 of the casing. The inner surface of the intake orifice 70 essentially represents a smooth continuation of a conically widened end section of the intake tube 18, which is mounted on the lower part 12 of the casing and sealed by means of a seal 72, and also located there with an axial peripheral section 74 by means of a circular locating rib 76.

An intermediate channel 78 is provided in the bottom of the upper part 12 of the casing axially above the outlet ends of the compressor vanes 64. The depth of the channel 78 increases in proportion to its angular dimension in the direction of a coplanar connecting channel 80, which leads outward to an inlet section 82 of the first side channel 44.

Figure 1:
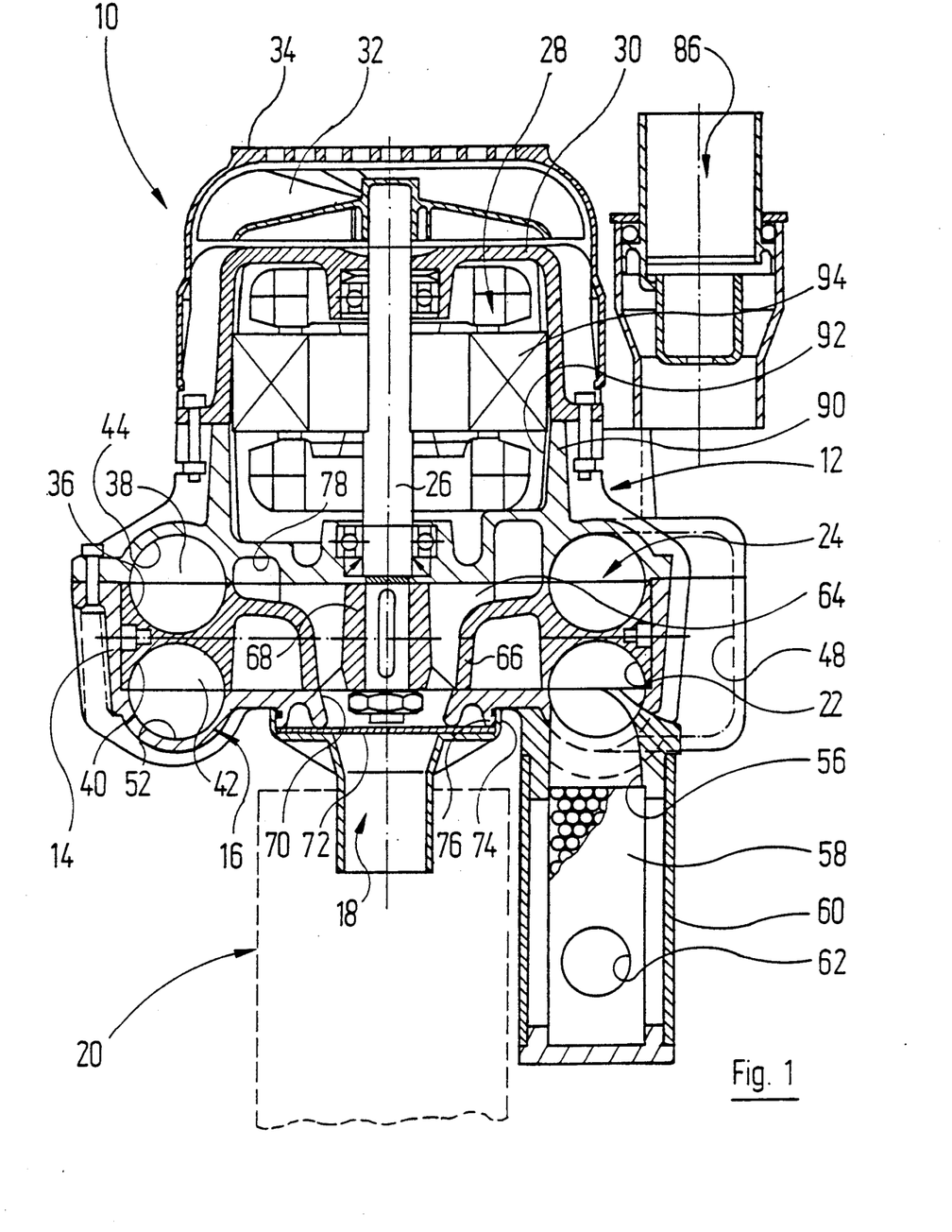
FIG. 1: an axial section through a two-stage side-channel suction device with its intake orifice positioned on the central axis of the casing and an additional intake side compressor and airstream diverting stage, which is integral with the rotor.
Figure 2:
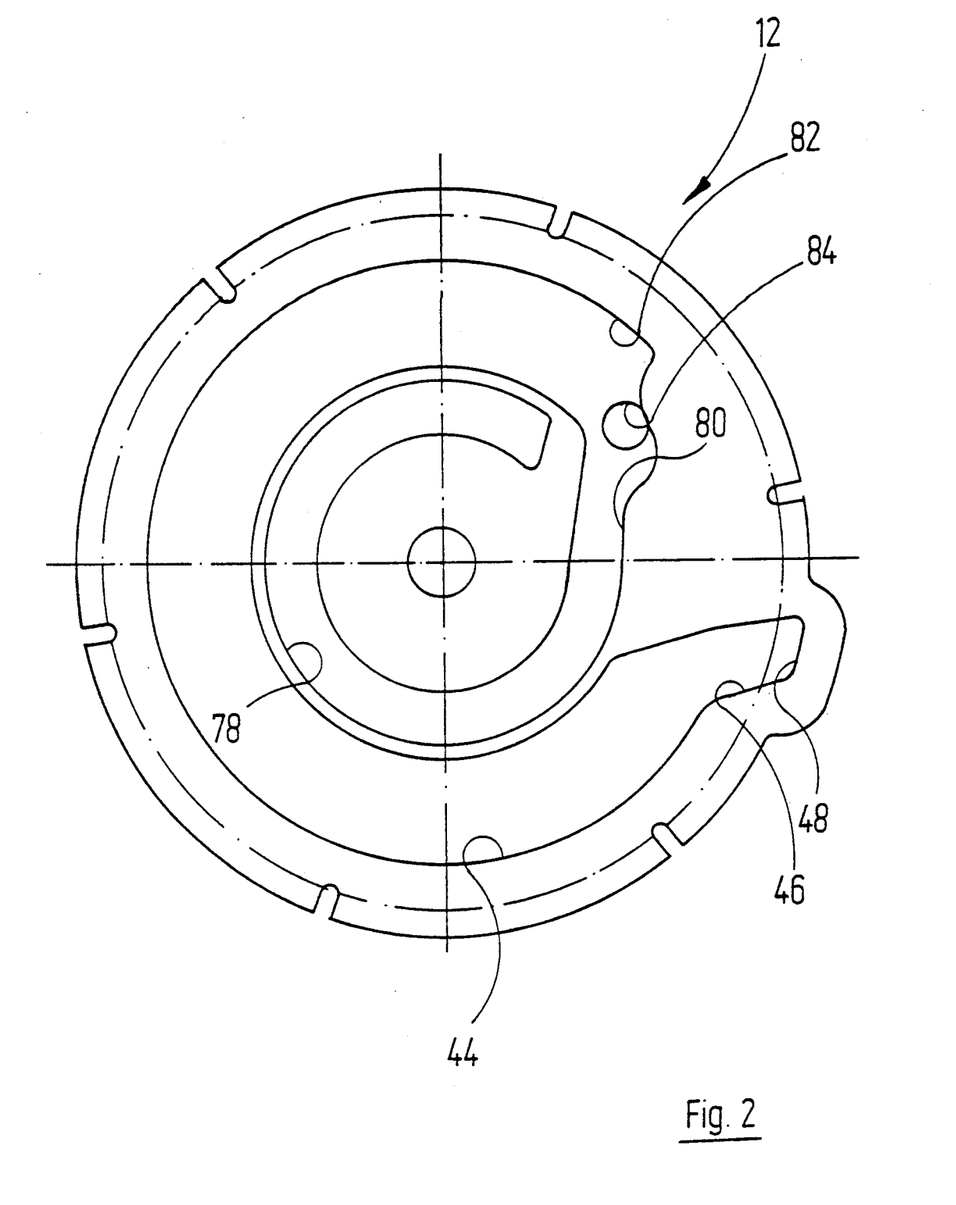
FIG. 2: a view of the underside of the upper part of a casing of the suction device of FIG. 1.
Figure 3:
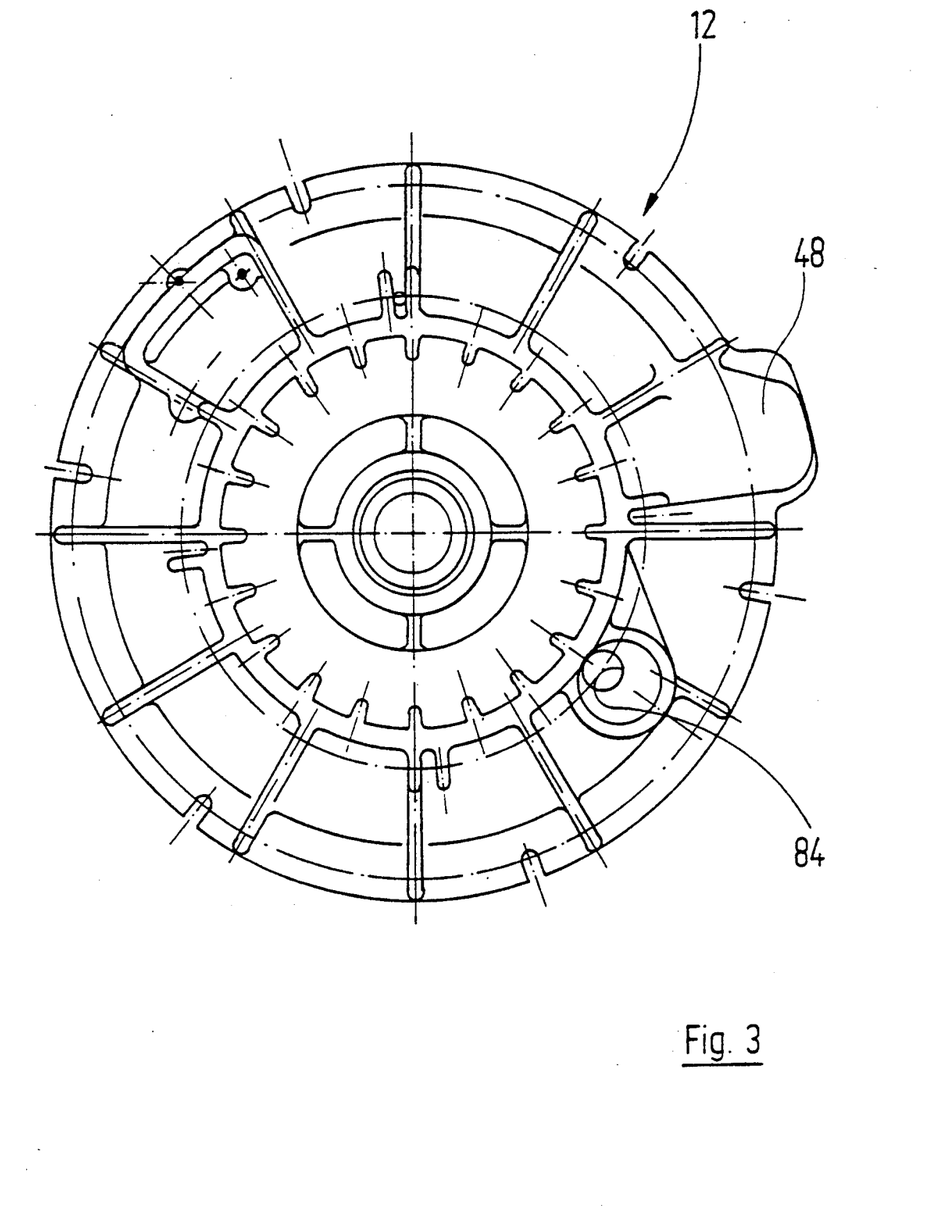
FIG. 3: a view of the top of the upper part of the casing of the suction device.
Figure 4:
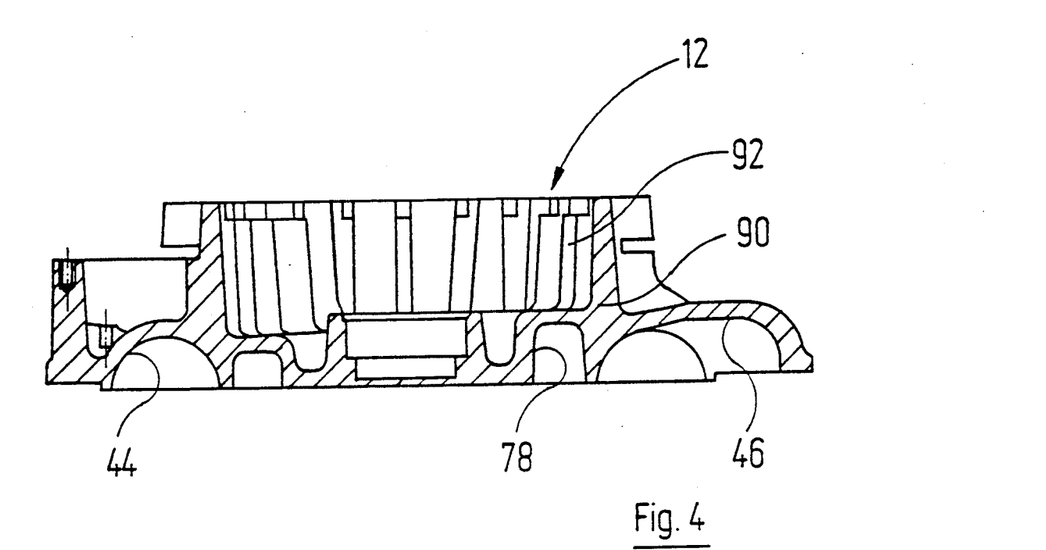
FIG. 4: an axial section through the upper part of the casing of the suction device in the plane of an axial connecting channel in the casing.
Figure 5:
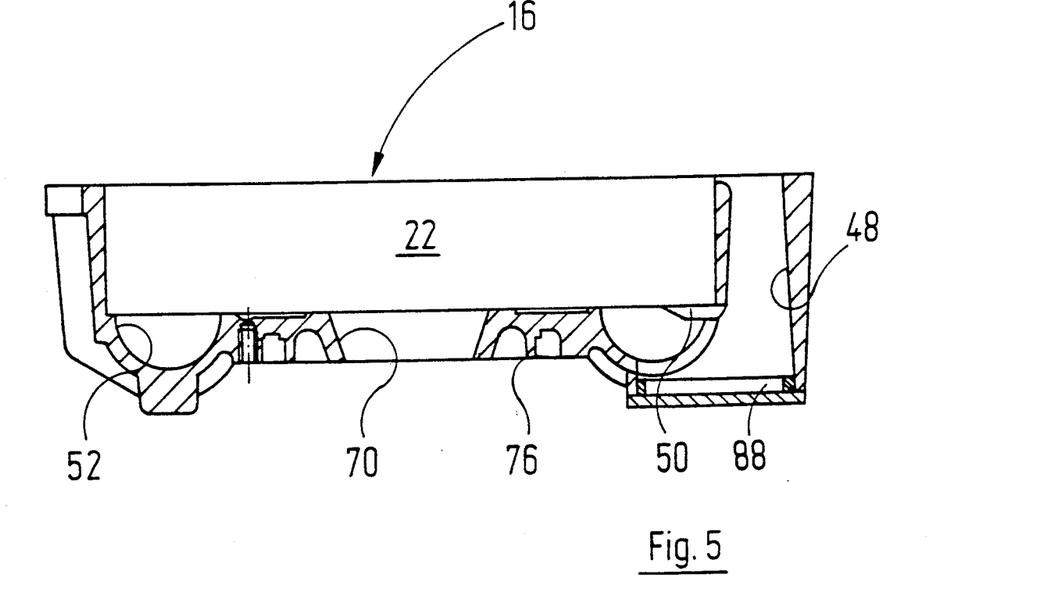
FIG. 5: an axial section through the lower part of the casing of the suction device in the same section plane as that in FIG. 4.
Figure 6:
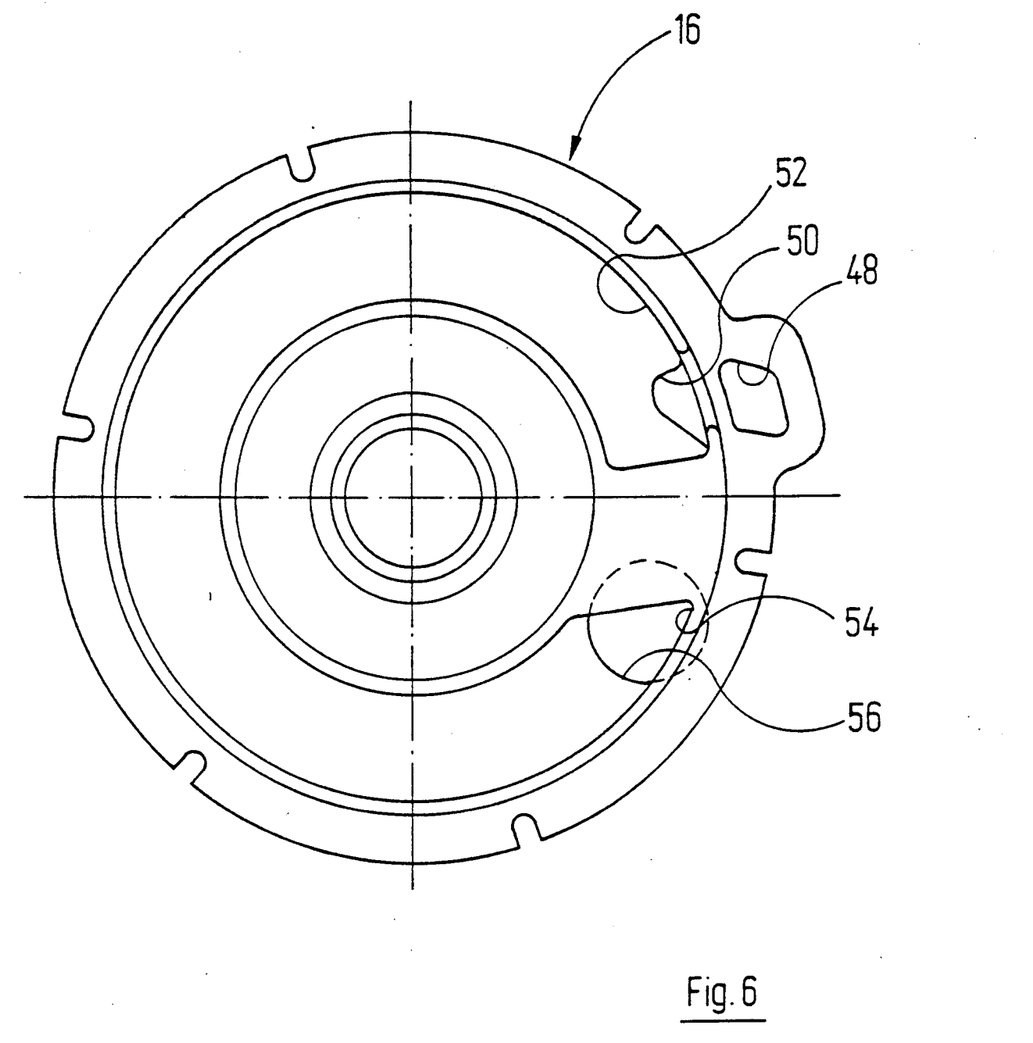
FIG. 6: a view of the upper side of the lower part of the casing of the suction device.
Figure 7:
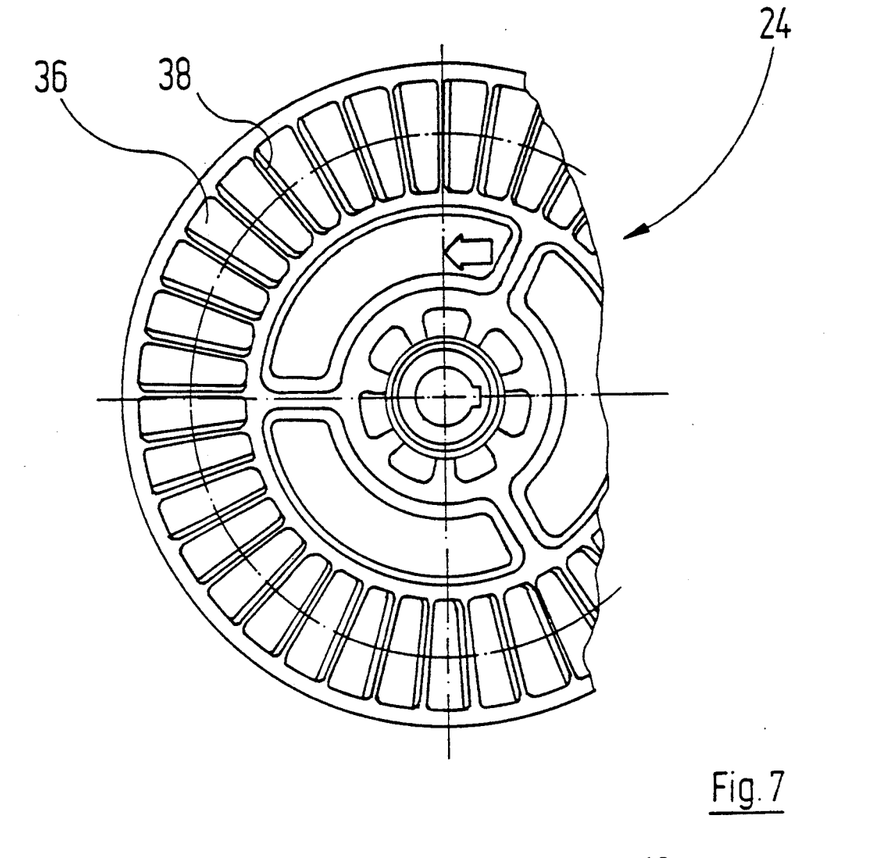
FIG. 7: a view of the lower side of the rotor of the suction device.
Figure 8:
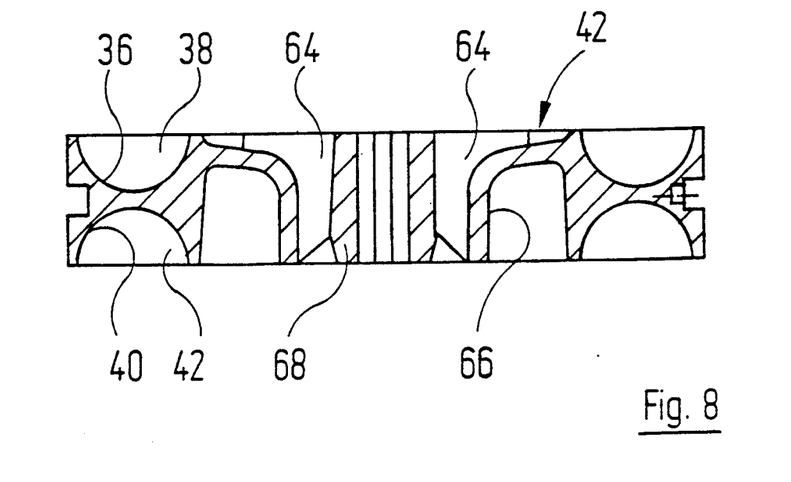
FIG. 8: an axial section through the rotor of the suction device.
Figure 9:
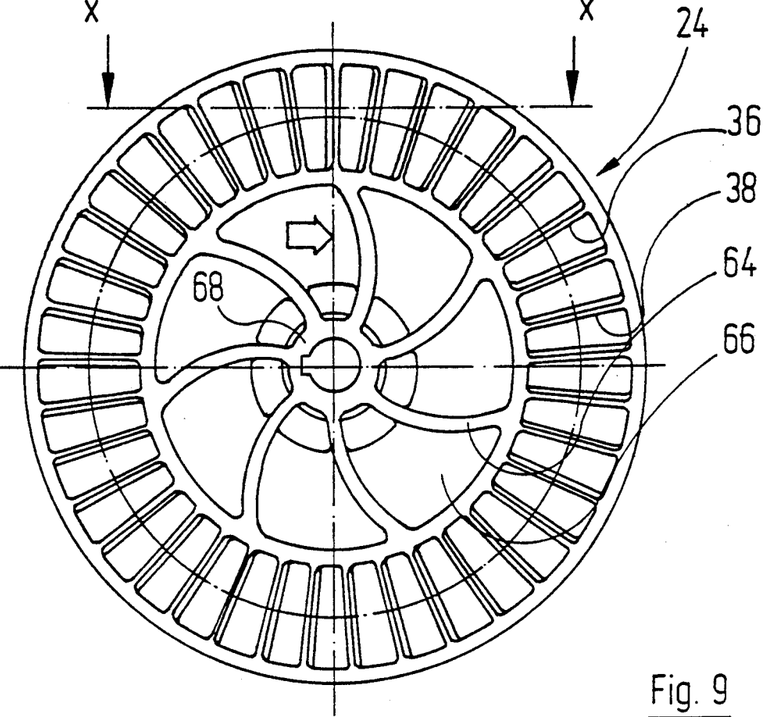
FIG. 9: a view of the upper side of the rotor of the suction device.

The connecting channel 80 is connected to an axially parallel secondary air channel 84, to which is joined a secondary air control unit 86, as indicated diagrammatically in FIG. 1. By means of the latter, and bypassing the compressor input stage formed by the compressor vanes 64, secondary air can be fed direct to the intake of the two-stage side-channel compressor, which is formed by the compressor vanes 38, 42 and the side channels 44, 52.

As is clear from the above description and also directly from an examination of FIG. 1, neither the axial nor the radial dimensions of the suction devices are increased by the provision of the compressor vanes 64 in the central area of the rotor 24. This central area of the rotor section 24 makes possible the provision of a central intake tube and the diversion of the intake air to the intake disposed radially outward of the two-stage side-channel compressor without any pressure losses as a result of the diversion, since the latter are balanced or even overcompensated by the compressor vanes 64.

As can also be seen from the drawing and the above description, the casing of the suction device consists of only two parts 12 and 16, which can easily be produced by casting. In order to ensure that the two-part form is sufficient in all cases, the axial connecting channel 48 is formed in the peripheral wall 14 as a channel open at the bottom and closed by a plug 88.

An upper wall 90 running in the direction of the circumference in the upper part 12 of the casing forms together with the covering wall of the casing part 12 a lower part of the motor casing. Locating ribs 92 project radially inward from the wall 90, which in the unmachined form of the cast casing part 12 are oversize and are then machined down to their final dimensions in such a way that they accept the stator 94 of the electric motor 28 so as to be interlocking. By machining the locating ribs 92 to different dimensions, the wall 90 can form the lower part of a motor casing for electric motors of different outputs.

I claim:
1. A suction device, especially for use in dentistry, having three series connected compressor stages comprising
 (a) a shaft (26) connectable to an electric motor (28);
 (b) a rotor (24) mounted on said shaft (26), which rotor is formed with two parallel end faces, each of which is provided with side-channel compressor vanes (38, 42) adjacent to the periphery of the rotor;
 (c) a casing (12, 16) defining a disc shaped rotor chamber having parallel end faces cooperating with the rotor (24) in essentially fluid tight manner to form first and second side-channels (44, 52) with the end faces of the rotor chamber, each side channel having an intake section and an outlet section;
 (d) an axial connecting channel (48) connecting the outlet section of the first side-channel to the inlet section of the second side-channel, the outlet section of the second side-channel being connected to an outlet orifice (62) of the casing (12, 16), while the intake section of the first side-channel (36) communicates with an inlet orifice (70) of the casing (12, 16);
 (e) the rotor (24) having a central hub portion (68) that surrounds said shaft (26), guide wall (66) annularly spaced from the hub portion and radially flaring towards said first side-channel (36) so as to form an axial passageway extending completely through the rotor (24), compressor vanes (64) mounted entirely within the annular space extending between the hub portion (68) and said guide wall (66); and
 (f) a first end face of said casing (12) being formed with an intermediate channel (78) that is aligned with an opposing end portion of the guide wall (66) and having a radially outwardly extending connec- tion section (80) communicating with the first side-channel (36).

2. A suction device according to claim 1 wherein the compressor vane arrangement (64) comprises compressor vanes whose direction of extension has a radial component.

3. A suction device according to claim 2 wherein the compressor vanes (64) are curved.

4. A suction device according to claim 1 wherein the compressor vanes (38, 42) formed by cutaways (36, 40) in the faces of the rotor (24) have a contour tapering rearwardly with respect to the direction of rotation.

5. A suction device according to claim 1 wherein the connecting channel (80) is connected to a subsidiary air channel (84) leading to the outer surface of the casing (12, 16).

6. A suction device according to claim 1 wherein the intermediate channel (78) has a width which is constant in the circumferential direction and a depth which increases towards the outlet end in proportion to the angular extension.

7. A suction device according to claim 1 wherein the rotor (24) is overhung mounted on the end of the shaft (26).

* * * * *